United States Patent [19]
Suzuki et al.

[11] Patent Number: 5,520,193
[45] Date of Patent: May 28, 1996

[54] BLOOD COLLECTING NEEDLE WITH VEIN INDICATOR

[75] Inventors: Issei Suzuki, 3211-17 Fukami, Yamato-shi, Kanagawa-ken; Hiroyasu Misawa; Kosei Misawa, both of Tokyo, all of Japan

[73] Assignees: Issei Suzuki, Kanagawa; Misawa Medical Industry Co., Ltd., Tokyo, both of Japan

[21] Appl. No.: 199,747

[22] Filed: Feb. 22, 1994

[30] Foreign Application Priority Data

Feb. 22, 1993 [JP] Japan .................................. 5-072743
Dec. 17, 1993 [JP] Japan .................................. 5-318253

[51] Int. Cl.6 ........................... A61B 5/00; A61M 1/00; A61M 5/32
[52] U.S. Cl. .................. 128/764; 604/274; 604/126; 604/900
[58] Field of Search ..................... 604/164, 168, 604/272, 274, 900, 122, 126, 190; 128/760, 763, 764, 766

[56] References Cited

U.S. PATENT DOCUMENTS

| | | | |
|---|---|---|---|
| 2,697,438 | 12/1954 | Hickey | 604/274 |
| 3,308,822 | 3/1967 | De Luca | 604/274 |
| 3,500,821 | 3/1970 | Ogle | 128/764 |
| 3,886,930 | 6/1975 | Ryan | 128/764 |
| 3,906,932 | 9/1975 | Ayres | 604/274 X |
| 4,416,290 | 11/1983 | Lutkowski | 128/764 |
| 4,416,291 | 11/1983 | Kaufman | 128/766 |
| 4,444,203 | 4/1984 | Engelman | 128/764 |
| 4,561,445 | 12/1985 | Berke et al. | 128/642 |
| 4,679,571 | 7/1987 | Frankel et al. | 128/764 |
| 4,808,170 | 2/1989 | Thornton et al. | 604/274 |
| 5,222,502 | 6/1993 | Kurose | 128/763 |
| 5,242,411 | 9/1993 | Yamamoto et al. | 604/167 |
| 5,354,537 | 10/1994 | Moreno | 422/100 |

*Primary Examiner*—John D. Yasko
*Assistant Examiner*—Adam J. Cermak
*Attorney, Agent, or Firm*—Larson and Taylor

[57] ABSTRACT

A needle assembly for evacuated blood collection tubes or containers comprises a single needle cannula, a needle cannula support made of a translucent or transparent material provided on the middle portion of the needle cannula, a blood flow confirmation passage formed in the interior of the needle cannula support and communicating with one end of the needle cannula, said one end being covered with an elastomeric resilient cap, and an air-permeable, blood repellant plug provided at an opening end of the passage.

6 Claims, 7 Drawing Sheets

BLOOD COLLECTING NEEDLE WITH VEIN INDICATOR

BACKGROUND OF THE INVENTION

The present invention relates to a needle assembly for evacuated blood collection tubes or containers, one end of which needle is inserted into the vein of a blood examinee, and the other end of which is adapted to be communicated with the interior of a evacuated blood collecting container so as to be able to collect blood in an amount responsive to the negative pressure in said container.

A known needle assembly of this kind is illustrated in FIG. 1. In this device, a needle cannula support A is secured to the middle portion of a stainless needle cannula B, and one end of the needle cannula support A is provided with a rubber cap C for covering one end of the needle cannula B. With such kind of needle assembly, the other end, i.e. the tip of the needle cannula B, is inserted into the vein of a blood examinee and a blood collection container is fitted over rubber cap C and communicating onto the other end of the needle cannula so as to communicate with the interior of the blood collection container. Blood entering the collection container provides a first indication that the needle has accurately entered the vein of the blood examinee. If it is necessary to reinsert the needle in order to draw blood, the negative pressure pre-set in the blood collection container may be released resulting in an inability to collect a desired amount of blood or the need to employ a further blood collection tube.

To remove such demerits, a variety of needle assemblies have been proposed that are constructed in such a way that when inserted into the vein of the blood examinee a flow-out of blood can be confirmed. One known example is such that a needle cannula is divided into two sections, one of which is to be inserted into the vein and the other to be inserted into a evacuated blood collection container. A member connecting these two needle sections is provided with a transparent blood flow passage, and it is confirmed through this passage whether the blood is flowing or not. In another known example, the middle portion of a needle cannula is bored with a hole which is circumferentially formed with a blood flow confirmation chamber.

In the known needle assembly where the needle cannula is constituted by two needle sections, the member connecting the two needle sections requires a lot of components whereby manufacturing steps and cost increase. Moreover, unless the air not only inside the needle but also in the transparent blood flow passage within the member connecting the two needle sections flows out, the blood does not flow, so that the structure needed to solve these problems becomes complicated.

On the other hand, according to a needle assembly where the needle cannula is bored with a hole which is circumferentially formed with a blood flow confirmation chamber, the confirmation chamber must be retained under negative pressure or released to the outside, and therefore as in the above case, the structure becomes complicated and the manufacturing cost increases.

Furthermore, such kinds of blood collection needle assemblies are used for collecting multiple samples of blood from a blood examinee, ordinarily changing the blood collection container, and each time a sample of blood is collected, the rubber cap at one end of the needle cannula is punctured. Generally, the tip of a needle is obliquely cut and the tip point is sharpened (lancet-shaped). However, since the tip point is positioned at the outer periphery of a needle cannula, it is feared that in manufacturing needle assemblies for blood sampling the rubber cap might be impaired when it is mounted over the needle tip. Conventionally, therefore, the sharpened tip point is bent toward the center axis of the needle cannula or obliquely cut while retaining a round point shape. Needles having such bent tips substantially decrease the danger of impairing the rubber cap when the cap is mounted in manufacturing the needle assemblies. On the other hand, however, the rubber cap is apt to be hooked by a bent tip point when the cap is returned to its original position when a blood collection container is disengaged from the needle. Moreover, the bending step increases manufacturing cost. With a rounded point, the cutting opening of the rubber cap becomes wider when punctured with a needle. Accordingly, when repeatedly punctured by other evacuated blood collection tubes, the rubber cap tends to lose its sealing property whereby such a rubber cap is not suited for repeated sampling of blood.

Furthermore, these needle assemblies are disposable so that it is desired to provide them at as low a cost as possible. It is further required to guarantee safe and certain functioning so that the user such as doctor or nurse may not directly contact blood when blood is collected.

SUMMARY OF THE INVENTION

The object of the present invention is therefore to provide a needle assembly for evacuated blood collection tubes or containers, which is easy and safe to use while solving the forementioned problems, which is of simple structure, and which can be manufactured at low cost.

In order to achieve the above objects, a needle assembly for use with evacuated blood collection tubes or containers according to the present invention includes a needle cannula one end of which, in use, is adapted for insertion into the vein of a blood examinee and the other end into a evacuated blood collection container, a needle cannula support mounted at the middle portion of said needle cannula, and an elastomeric resilient cap mounted at the other end of said needle cannula. In use, the blood collection container is mounted liquid-tight to the needle cannula support from the other end side of the needle cannula, which side is fixed with the cap, and when piercing the elastomeric resilient cap, the other end of the needle cannula is communicated with the interior of the blood collection container. The present needle assembly is characterized in that the needle cannula support is made of a translucent or transparent material and is fixed liquid-tight to the needle cannula at the one end side of the cannula, the needle cannula support is provided with a longitudinal passage opening to the other end side of the needle cannula along the outer periphery of the cannula, and with a radial passage extending radially from the inward end of said longitudinal path and communicating with the outside, and at least one air-permeable, liquid repellant or impermeable plug is anchored in the radial path.

Preferably, the longitudinal path in the needle cannula support may be circularly formed around the needle cannula.

Alternatively, the longitudinal path in the needle cannula support may be oval-shaped in section, and it may be constructed to be brought into partial contact with the outer periphery of the needle cannula or it may consist of a plurality of paths extending along the longitudinal direction of the outer periphery of the needle cannula.

Further, preferably, one end of the radial path in the needle cannula support may communicate with the inward end of said longitudinal path and the other end may open to the outside to allow this open end to be provided with the air-permeable, liquid liquid repellant or impermeable plug.

The air-permeable, blood repellant plug preferably comprises a paper mass. Instead, it may be constituted by a synthetic resinous mass.

Furthermore, the inner edge of the open outer end of said radial path may be outwardly tapered.

Furthermore, preferably, the end of the needle cannula which is covered with the elastomeric resilient cap, may extend in parallel with the axis of the needle cannula and may be provided with a pointed tip positioned within the outer circumference of the needle cannula.

In the needle assembly according to the invention, the needle cannula support made of a translucent or transparent material may be provided at the middle portion of a single needle cannula, and the blood flow confirmation passage is formed within the needle cannula support. The confirmation passage communicates with the tip point at the end side of the needle cannula which is covered with the elastomeric resilient cap. The open end of said passage is provided with an air-permeable, liquid repellant plug, and therefore it is possible to easily confirm whether the needle has accurately entered the vein of a blood examinee when blood is collected. When the needle cannula is then inserted into a evacuated blood collection container (substantially tube) the needle cannula itself is blocked from communication with the blood flow confirmation passage within the needle cannula support whereby it is possible to collect a desired amount of blood through the needle cannula.

Alternatively, by employing a paper mass as the air-permeable, liquid repellant plug it becomes possible to construct a needle assembly without substantially increasing manufacturing cost. Moreover, since the liquid repellant plug is made of a paper mass, the needle assembly can be easily dealt with after use, and in addition to its operational safety it will also be advantageous from the viewpoint of preventing environmental contamination when the needle assembly is disposed of.

Furthermore, because of the shape of the tip of the needle which is covered by the elastomeric resilient cap, extends in parallel with the axis of the needle cannula and has a point which is within the outer circumference of the needle cannula, the elastomeric resilient cap does not tend to be hooked when mounted in the assembling process of the needles. Additionally, even if evacuated blood collection containers are repeatedly engaged and disengaged, the cutting opening neither broadens nor is hooked whereby the sealability of the cap can be sufficiently retained and operability improved.

BRIEF DESCRIPTION OF THE DRAWINGS

The invention will now be described more in detail, by way of embodiments, with reference to the accompanying drawings in which.

DETAILED DESCRIPTION

Figure 1:
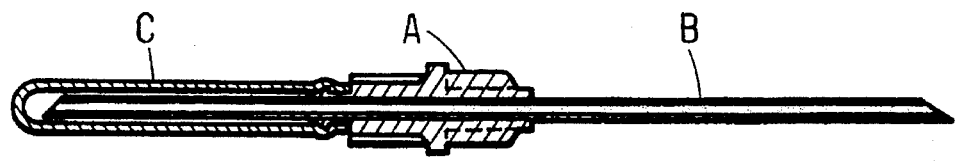
FIG. 1 is a schematic diagram illustrating one example of a known needle assembly.
Figure 2:
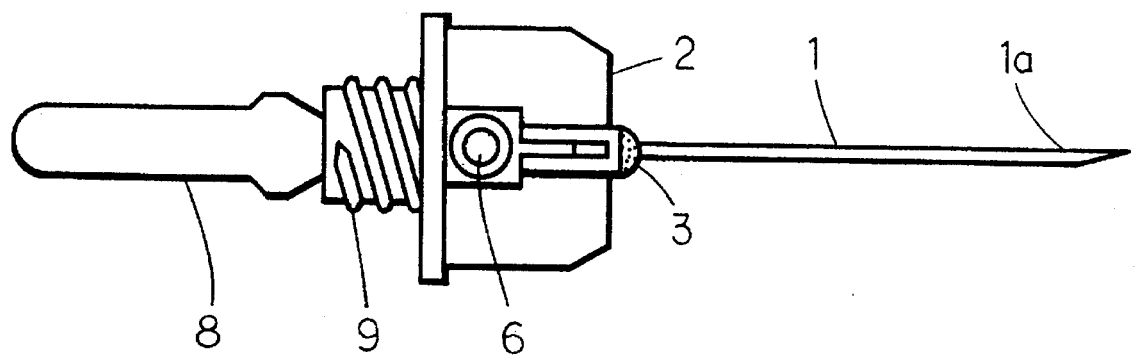
FIG. 2 is a schematical front view of the needle assembly for evacuated blood collection tubes according to one embodiment of the present invention.
Figure 3:
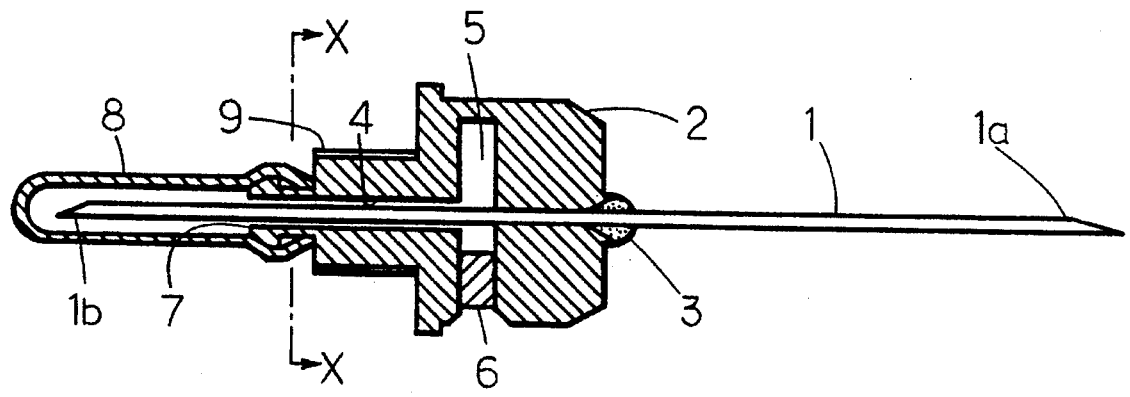
FIG. 3 is a longitudinal section when viewed from the left of the needle assembly illustrated in FIG. 2.
Figure 4:
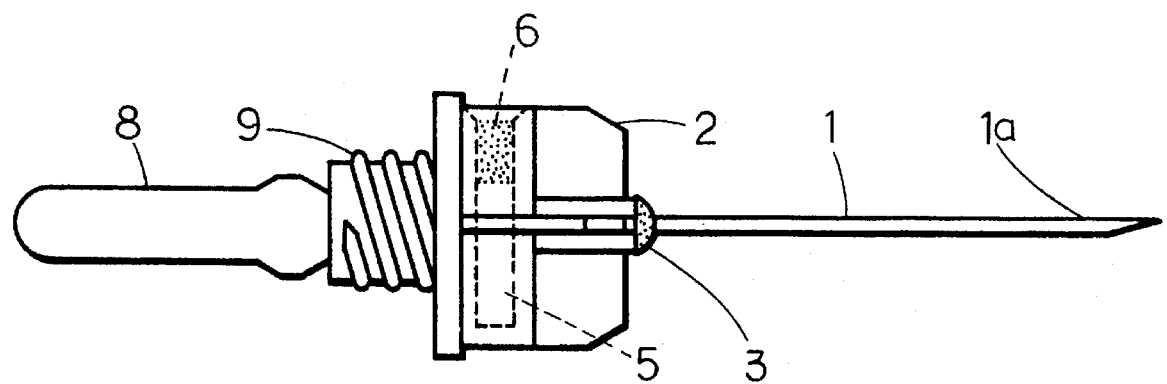
FIG. 4 is a side view when viewed from the right of the needle assembly illustrated in FIG. 2.
Figure 5:
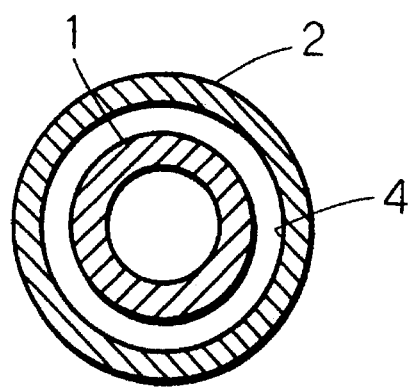
FIG. 5 is an enlarged partial cross-section taken along arrow X—X of FIG. 3.

Referring to the drawings, FIGS. 2–5 illustrate one embodiment of the present invention. The reference numeral 1 designates a stainless needle cannula, one end 1a of which is formed, in use, to be inserted into the vein of a blood examinee, and the other end 1b to be inserted into a evacuated blood collection container (substantially tube) not shown. A single needle cannula support 2 made of a transparent material is secured liquid-tight, with an adhesive 3, as shown, to the middle portion of the needle cannula 1 at the side of said one end 1a. Further, as shown in FIG. 3, the needle cannula support 2 is internally formed with a longitudinal passage 4 opening at the other end 1b side of the needle cannula 1 along the outer circumference of said cannula and forming a path for the flow of confirmation blood, and with a radial passage 5 having a circular shape in section, said radial path extending radially and outwardly from the inward end of said longitudinal passage 4 and communicating with the outside. As illustrated in FIG. 5, the longitudinal passage 4 is annularly formed in the circumference of the needle cannula 1. The inner edge of the opening end of said radial passage 5 is tapered outwardly. The inside of the radial path is anchored with a mass 6 made of paper or synthetic resin, said mass serving as an air-permeable, liquid repellant plug which prevents blood from leaking to the outside. Paper mass 6 may be a paper having a suitable thickness coated with a starch component such as corn starch to an extent ranging from several percent to 30 percent, the paper being rolled cylindrically, and then dried.

The opening end of the longitudinal passage 4 of said needle cannula support 2 is formed with a flange 7 which anchors an elastomeric resilient cap 8 that sealingly covers the other end 1b side of the needle cannula 1. Cap 8 is composed of an elastomeric resilient material such as rubber, and the receiving portion of the blood collection container, in use, is engaged with a threaded portion 9.

Figure 6:
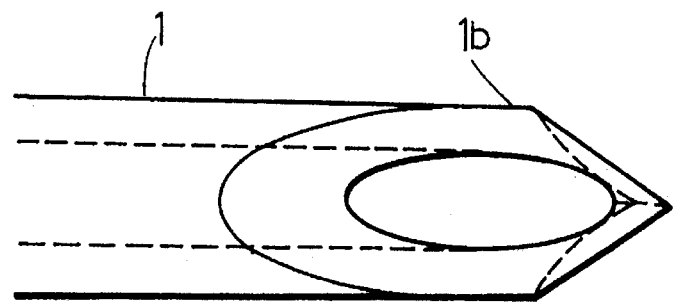
FIG. 6 is an enlarged schematic front view of the tip of the needle cannula of the needle assembly illustrated in FIG. 2, said tip being at the side covered with the elastomeric resilient cap.
Figure 7:
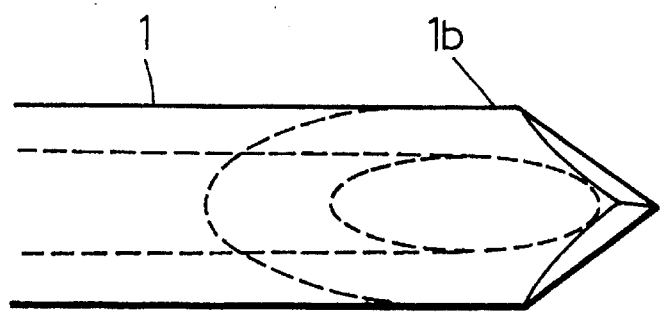
FIG. 7 is a schematic rear view of the needle tip illustrated in FIG. 6.
Figure 8:
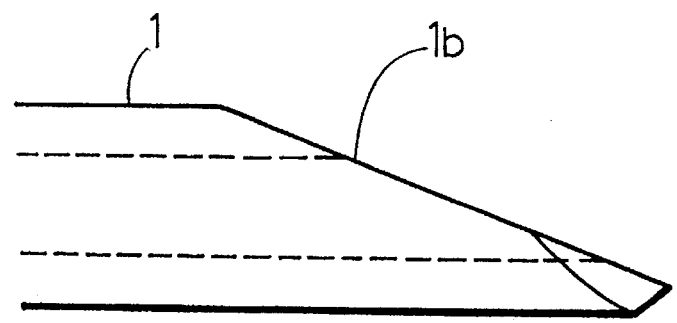
FIG. 8 is a schematic side view of the needle tip illustrated in FIG. 6.

As illustrated in FIGS. 6–8, the tip of the other end 1b of the needle cannula 1 is pointed by an oblique cut across its end as shown in FIG. 8 and by cuts at both sides of the oblique cut such that the pointed tip extends in parallel with the axis of the needle cannula, and such that the point is positioned more inwardly than the outer circumference of the needle cannula 1. Therefore, when the elastomeric resilient cap is mounted in the manufacturing procedure there is no longer a fear that the cap 8 might be hooked by the needle tip. On the other hand, the cap 8 is less damaged when a evacuated blood collection container is mounted or dismantled, and sealability can be sufficiently ensured even if the blood collection container are repeatedly replaced.

Figure 9:
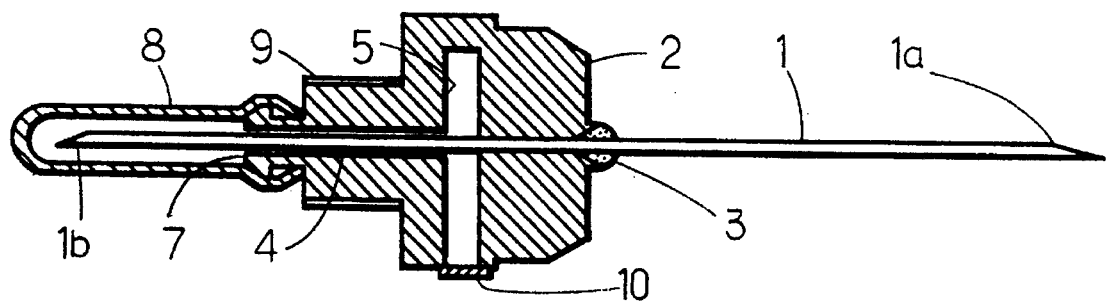
FIG. 9 is a schematic longitudinal section illustrating a modified embodiment of the invention.

FIG. 9 shows a modified embodiment of the present invention, wherein a paper or synthetic resinous, film-like plug 10 is adhered at the outside of the opening of the radial path 5.

Figure 10:
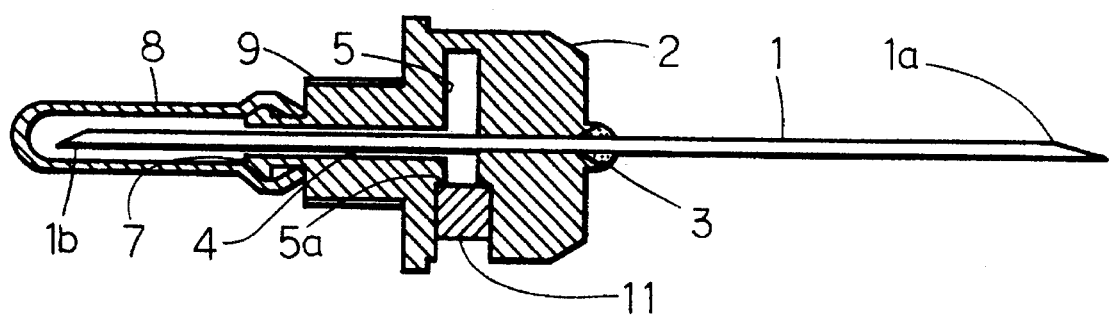
FIG. 10 is a schematic longitudinal section illustrating another embodiment of the invention.

FIG. 10 shows another embodiment of the invention, wherein the radial passage 5 arranged in the needle cannula 2 has a shoulder 5a near its opening, the portion of passage 5 outside shoulder 5a being made larger in diameter, and being fitted with a paper or synthetic resinous mass 11 serving as an air-permeable, blood repellant plug.

Figure 11:
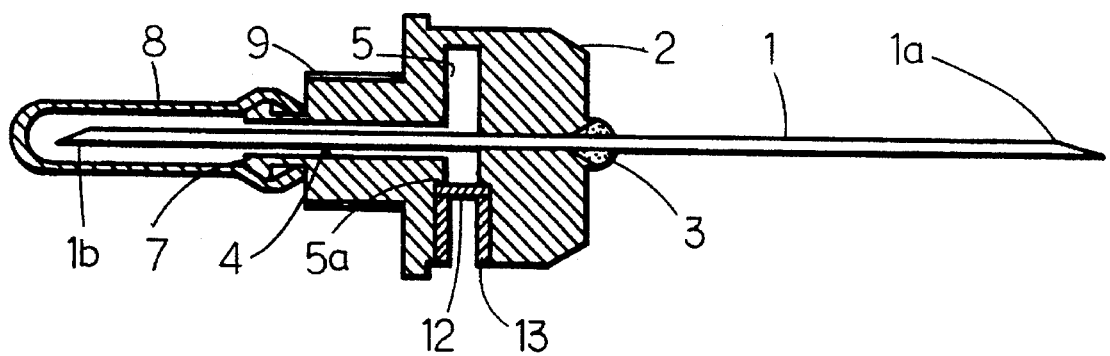
FIG. 11 is a schematic longitudinal section illustrating another modified embodiment of the invention.

FIG. 11 illustrates a modification of the embodiment shown in FIG. 10, in which the air-permeable, blood repellant plug comprises a paper or synthetic resinous, film-like plug 12 abutted against the shoulder 5a at the end of a cylindrical holding member 13 to which plug 12 is adhered. In such case, the film-like plug 12 may alternatively be adhered directly to the shoulder 5a in the radial passage 5.

Figure 12:
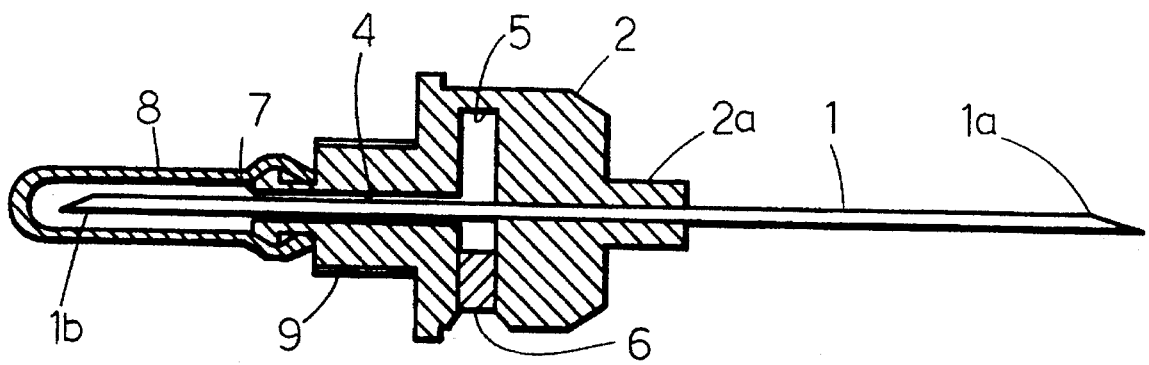
FIG. 12 is a schematic longitudinal section illustrating still another modified embodiment of the invention.

FIG. 12 illustrates still another modified embodiment of the invention, wherein one of the needle cannula support 2 protrudes as shown with the reference numeral 2a, and at that protruded end the needle cannula support 2 is secured by high-frequency melting to the needle cannula 1.

Figure 13:
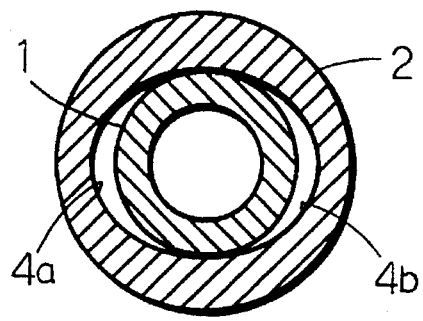
FIG. 13 is a view similar to FIG. 5 but illustrating another modified example of the essential portion of the needle assembly illustrated in FIGS. 2–5.
Figure 14:
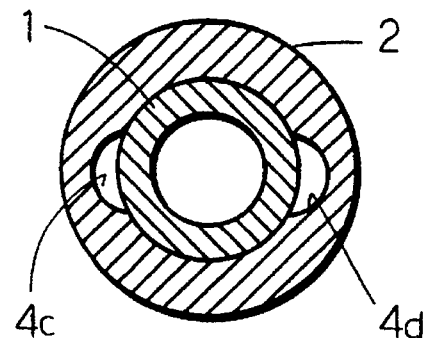
FIG. 14 is a view similar to FIG. 5 but illustrating a further modified example of the essential portion of the needle assembly illustrated in FIGS. 2–5.

FIGS. 13 and 14 illustrate modified examples of the longitudinal passage 4 formed in the needle cannula support 2. In FIG. 13 the longitudinal passage 4 is of oval shape in section, and it makes longitudinally a line contact at the shorter axis side with the outer periphery of the needle cannula 1 thereby forming at the longer axis side two passages 4a, 4b, each having a crescent shape in section. On the other hand, in FIG. 14, the needle cannula support 2 makes in the longitudinal direction an arc-like, surface contact with the outer periphery of the needle cannula 1 thereby partitioning the blood confirmation passage by two grooves 4c, 4d formed longitudinally in the needle cannula support 2.

Figure 15:
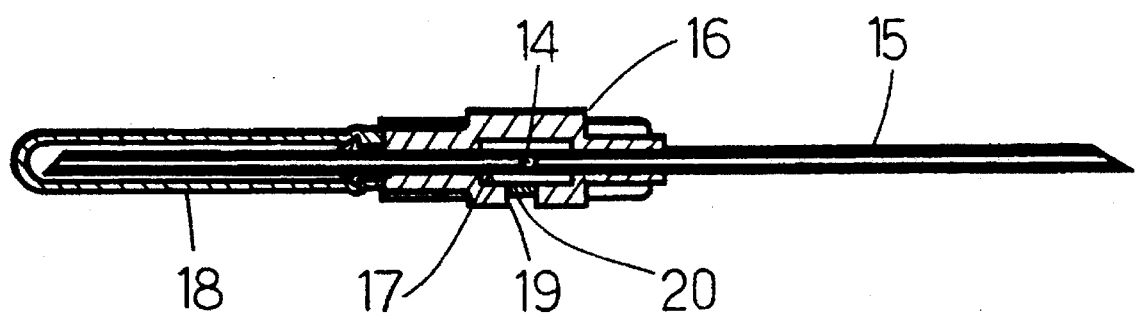
FIG. 15 is a schematic longitudinal section illustrating still another modified embodiment of the invention.

FIG. 15 illustrates still another modified embodiment of the invention in which a hole 14 is made at the middle portion of a needle 15, said middle portion is covered with a single translucent or transparent resinous cover or support 16, and a middle hollow portion 17 is provided in said support 16. A clearance is provided between the needle portion covered with a rubber cap 18 and the middle hollow portion 17. The needle 15 is sealingly fixed within the translucent or transparent resinous cover 16. On the other hand, the middle hollow portion 17 is provided with an opening 19 and opening 19 is provided with a water-repellant synthetic resinous body 20 which is used in the form of either a solid body or a membrane depending on use conditions.

Figure 16:
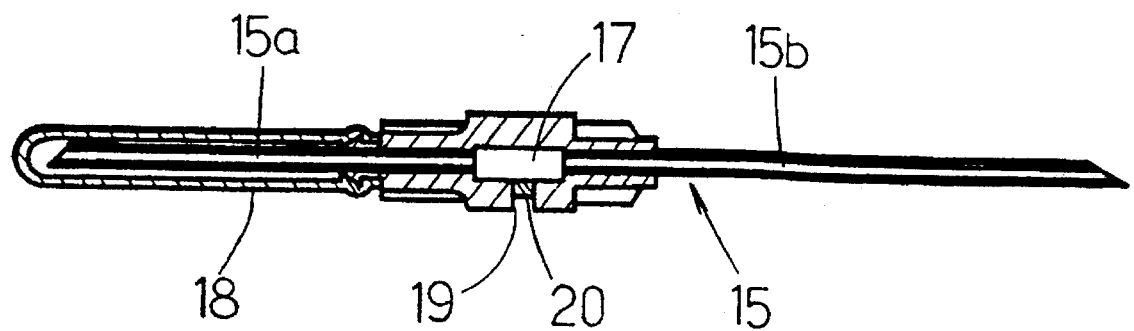
FIG. 16 is a schematic longitudinal section illustrating a modification of the embodiment of FIG. 15.

FIG. 16 illustrates a modification of the embodiment shown in FIG. 15, in which the needle 15 is separated into two needle portions 15a and 15b.

The resinous body 20 has properties that air permeates therethrough but blood or liquid does not. It is important that blood smoothly flows into the middle hollow portion 17 from the hole 14 and that the needle 15 at the rubber cap 18 side, when the end tip of the needle 15 has entered the vein of an upper arm of a blood examinee having normal blood pressure, the blood never flows to the outside of the resinous body 20, and that even if suction were carried out from the rubber cap 18 side in the evacuated blood collection tube or container, the outside air is never sucked in.

If, in use, the end tip of the needle 15 correctly enters the vein, blood flows out of the hole 14 thereby coloring in red the interior of the middle hollow portion 17, thus confirming that said end tip is inserted in the vein. This enables even an unskilled user to be able to collect blood easily with the needle assembly of the present invention.

When the end tip of the needle 15 correctly enters the vein of a blood examinee, blood flows into the middle hollow portion 17 of the resinous support 16, so that the correct insertion of the needle can be confirmed with unaided eyes. Then the rubber plug of the evacuated blood collection tube is pressed toward the needle side covered with the rubber cap, causing the blood to flow easily into the tube, whereby it is possible to collect blood with a single operation for a plurality of evacuated blood collection tubes.

A suitable air-permeable, blood repellant plug comprises paper coated with a starch component such as corn starch, rolled cylindrically into a cylinder (being 2.4 mm in diameter and 3.0 mm long), and dried. The air permeability of the paper cylinder was measured as described below.

Blood was put into a container (tube) sealed with a rubber plug, and the needle assembly was inserted into the rubber plug while retaining the pressure within the container at certain levels by altering the pressure range from 40.0 g/m$^2$ to 7.0 g/m$^2$ and observations were carried out for each of the pressure levels. The pressure gauge used was "HANDY MANOMETER" PG-100-101G (made by Copal Denski KK).

| Pressure in container (g/m$^2$) | Flow-in state of blood into needle cannula support 2 |
| --- | --- |
| 40.0 | Very good |
| 30.0 | Very good |
| 20.0 | Very good |
| 15.0 | Good |
| 10.0 | It took about one second |
| 7.0 | Hardly flowed-in |

Human blood is usually drawn from a vein, and venous pressure is different from arterial blood pressure, the latter being generally called blood pressure. Venous pressure varies principally in relation to the vertical height between the measuring region and the position of the examinee's heart. The following are the data as a result of having measured the venous pressure of 20 persons in their blood evacuating posture.

Pressure at the time of normal evacuation in a sitting posture: 65.0–73.0 g/m$^2$ Pressure at the time of normal evacuation in the supine posture: 50.0–60.0 g/m$^2$ In the above testing, 150.0 g/m$^2$ was the upper limit measured in the resisting pressure under which the air could be discharged and the blood could be stopped from flowing in case the liquid repellant plug absorbed the blood to expand.

It will be understood from this testing result that the needle assembly of the present invention is quite enough to be used if the venous pressure is 15.0 g/m² or higher, that it safely functions up to a pressure which is twice that of normal venous pressure, and that it therefore can be used in the range of normal venous pressure without any trouble.

In the embodiments illustrated in the drawings there is used, as the air-permeable liquid repellant plug, a paper coated with a starch component such as corn starch and the paper is dried in the form of film or mass, or a synthetic resinous material impregnated with starch component. However, a plug made of paper itself will be more advantageous from the viewpoint of manufacturing cost.

Alternatively, the air-permeable, liquid repellant plug can be provided as a double stacking.

Referring to the radial passage, it is possible that it radially pierces the needle cannula support, and that an air-permeable, liquid repellant plug may be provided at both of its ends.

As described above in detail, according to the present invention, a needle cannula support made of a translucent or transparent material is provided at the middle portion of a single needle cannula, a blood flow confirmation passage is formed within the needle cannula support, said passage communicating with one end of the needle cannula while said end is covered with an elastomeric resilient cap, and one opening end of said passage is provided with an air-permeable, blood repellant plug. When blood is drawn, it is capable of easily confirming by inserting the needle into the blood examinee's vein whether the needle is in correct insertion or not. Moreover, at the time of collecting blood into an evacuated blood collection container, the needle cannula itself communicates with only the blood collection container whereas it is shielded from the blood flow confirmation passage within the needle cannula whereby a desired amount of blood can be collected through the needle cannula. Accordingly, not only does practical blood collection operation become easier, but also the frequency of re-insertion of the needle can be reduced so as to lessen the examinee's discomfort.

Further, since the needle assembly for blood collection according to the invention employs a needle cannula support comprising a single moulding body, and since the air-permeable, liquid repellant plug can be made of paper, it is possible to provide the same without substantially increasing the manufacturing cost compared with conventional needle assemblies.

Furthermore, according to the vacuum needle assembly for blood collection of the invention, the end of the needle cannula, which is covered with the elastomeric resilient cap, extends in parallel with the axis of the needle cannula and is pointed in shape while the point is positioned within the outer periphery of the needle cannula, and therefore the cutting opening of said cap is neither broadened nor hooked so that the sealability of the elastomeric resilient cap can be sufficiently retained and the operability of the needle assembly can be improved.

Furthermore, even in the manufacturing procedure, only one constitutional component increases and the structure itself of the needle cannula support is not complicated, so that the needle assembly for evacuated blood collection tubes is structurally simplified compared with those conventionally proposed wherein the flow of blood can be confirmed, thereby reducing manufacturing cost.

What is claimed is:

1. A needle assembly for use with an evacuated blood collection container to draw blood from a blood examinee, said needle assembly comprising a needle cannula, one end of which is, in use, inserted into the vein of a blood examinee and the other end of which, in use, is inserted into a blood collection container, a needle cannula support mounted at the middle portion of the needle cannula, such that said one end of said needle cannula extends outwardly from a first side thereof and said other end of said needle cannula extends outwardly from an opposite side thereof, and an elastomeric resilient cap mounted on the cannula support over said other end of said needle cannula, said needle cannula support being a single body made of a translucent or transparent material, said one end of said needle cannula being fixed liquid-tight at said first side of the needle cannula, said support being provided with a longitudinal passage opening to said opposite side of the needle cannula support along the outer periphery of the cannula and extending to an inner end within said support, and being further provided with a radial passage extending radially from said inner end of said longitudinal passage and communicating with the outside, and at least one air-permeable, liquid repellant plug anchored in the radial passage, said longitudinal passage in the needle cannula support being of oval shape in section and being in partial contact with the outer periphery of the needle cannula.

2. A needle assembly for use with an evacuated blood collection container to draw blood from a blood examinee, said needle assembly comprising a needle cannula, one end of which is, in use, inserted into the vein of a blood examinee and the other end of which, in use, is inserted into a blood collection container, a needle cannula support mounted at the middle portion of the needle cannula, such that said one end of said needle cannula extends outwardly from a first side thereof and said other end of said needle cannula extends outwardly from an opposite side thereof, and an elastomeric resilient cap mounted on the cannula support over said other end of said needle cannula, said needle cannula support being a single body made of a translucent or transparent material, said one end of said needle cannula being fixed liquid-tight at said first side of the needle cannula, said support being provided with a longitudinal passage opening to said opposite side of the needle cannula support along the outer periphery of the cannula and extending to an inner end within said support, and being further provided with a radial passage extending radially from said inner end of said longitudinal passage and communicating with the outside, and at least one air-permeable, liquid repellant plug anchored in the radial passage, said permeable, liquid repellant plug being made of a paper mass.

3. A needle assembly for use with an evacuated blood collection container to draw blood from a blood examines, said needle assembly comprising a needle cannula, one end of which is, in use, inserted into the vein of a blood examines and the other end of which, in use, is inserted into a blood collection container, a needle cannula support mounted at the middle portion of the needle cannula, such that said one end of said needle cannula extends outwardly from a first side thereof and said other end of said needle cannula extends outwardly from an opposite side thereof, and an elastomeric resilient cap mounted on the cannula support over said other end of said needle cannula, said needle cannula support being a single body made of a translucent or transparent material, said one end of said needle cannula being fixed liquid-tight at said first side of the needle cannula, said support being provided with a longitudinal passage opening to said opposite side of the needle cannula support along the outer periphery of the cannula and extending to an inner end within said support, and being further provided with a radial passage extending radially from said inner end of said longitudinal passage and communicating with the outside, and at least one air-permeable, liquid repellant plug anchored in the radial passage, the bore of said other end of said needle cannula being substantially straight throughout its length and having a sharpened point formed without bending the needle cannula, said point being positioned within the outer periphery of the needle cannula, the longitudinal passage in the needle cannula support being of oval shape in section and being in partial contact with the outer periphery of the needle cannula.

4. A needle assembly as set forth in claim 3, wherein the end of said radial passage which communicates with the outside is tapered outwardly.

5. A needle assembly for use with an evacuated blood collection container to draw blood from a blood examines, said needle assembly comprising a needle cannula, one end of which is, in use, inserted into the vein of a blood examines and the other end of which, in use, is inserted into a blood collection container, a needle cannula support mounted at the middle portion of the needle cannula, such that said one end of said needle cannula extends outwardly from a first side thereof and said other end of said needle cannula extends outwardly from an opposite side thereof, and an elastomeric resilient cap mounted on the cannula support over said other end of said needle cannula, said needle cannula support being a single body made of a translucent or transparent material, said one end of said needle cannula being fixed liquid-tight at said first side of the needle cannula, said support being provided with a longitudinal passage opening to said opposite side of the needle cannula support along the outer periphery of the cannula and extending to an inner end within said support, and being further provided with a radial passage extending radially from said inner end of said longitudinal passage and communicating with the outside, and at least one air-permeable, liquid repellant plug anchored in the radial passage, the bore of said other end of said needle cannula being substantially straight throughout its length and having a sharpened point formed without bending the needle cannula, said point being positioned within the outer periphery of the needle cannula, said air-permeable, liquid repellant plug being made of a paper mass.

6. A needle assembly as set forth in claim 5, wherein the end of said radial passage which communicates with the outside is tapered outwardly.

* * * * *